United States Patent [19]

Reed

[11] Patent Number: 4,655,217
[45] Date of Patent: Apr. 7, 1987

[54] METHOD AND APPARATUS FOR DISABLING VEIN VALVES IN-SITU

[76] Inventor: Matt H. Reed, 22 Thatcher St., Hyde Park, Mass. 02136

[21] Appl. No.: 786,658

[22] Filed: Oct. 11, 1985

[51] Int. Cl.$^4$ ............................................. A61F 17/32
[52] U.S. Cl. .................................. 128/305; 128/303 R
[58] Field of Search .................. 128/303 R, 305, 354, 128/311

[56] References Cited

U.S. PATENT DOCUMENTS

| | | | |
|---|---|---|---|
| 3,749,085 | 7/1973 | Willson et al. ........................ | 128/305 |
| 3,837,345 | 9/1974 | Matar ................................... | 128/305 |
| 4,467,802 | 8/1984 | Maglanka ............................. | 128/354 |
| 4,493,321 | 1/1985 | Leather ............................. | 128/303 R |

FOREIGN PATENT DOCUMENTS

| | | | |
|---|---|---|---|
| 2305815 | 8/1974 | Fed. Rep. of Germany ... | 128/303 R |
| 3007165 | 9/1981 | Fed. Rep. of Germany ...... | 128/305 |
| 3313325 | 10/1984 | Fed. Rep. of Germany ...... | 128/305 |
| 537676 | 1/1977 | U.S.S.R. .............................. | 128/305 |

*Primary Examiner*—Gene Mancene
*Assistant Examiner*—J. Hakomaki
*Attorney, Agent, or Firm*—Bromberg, Sunstein & McGregor

[57] ABSTRACT

An apparatus is provided for disabling valve cusps within a vein. A flexible guide tube of a diameter substantially smaller than that of a vein has at least one retractable wire hook for ensnaring a valve cusp within the vein. The wire hook may be continuously moved from a retracted position against the tube end to an extended position toward a vein wall. Valve cusps are trapped by a narrow gap at the end of the hook, and are disabled by pulling the sharp point of the hook through them.

14 Claims, 12 Drawing Figures

METHOD AND APPARATUS FOR DISABLING VEIN VALVES IN-SITU

DESCRIPTION

1. Field of Invention

The present invention relates to surgical cannular apparatus, and in particular to valvulotomes for disabling vein valves.

2. Background Art

Atherosclerosis is a common arterial disease in which the buildup of fatty deposits, known as plaques, in arterial walls can result in severe constriction of blood flow. In treating atherosclerosis surgically, the obstructed portions of affected arteries can be bypassed with alternative vessels that are attached, or grafted, directly to the artery at sites above and below the obstruction. While it has been found that the most suitable conduit for such purposes is a nontraumatized, nondissected in-situ vein (usually the saphenous vein of the leg), the valves of these veins—a series of delicately thin but highly tensile cusps—normally used to keep venous blood flowing toward the heart, must first be removed so that arterial blood can now flow down the vein and back down into the artery. Among the devices and procedures which have been developed thus far for removing these vein valves, many involve significant trauma to the vein. The result in some patients has been the loss of the bypass conduit, death of the foot or leg and, in some cases, death of the patient. The invention described herein is less traumatic to the vein and will make significantly less surgery necessary than is the case with many current techniques and devices.

One early procedure developed for removing vein valves was to incise the skin over the entire length of the saphenous vein (i.e., from the groin to the ankle), and then to incise the vein at each valve site. Once exposed, the valve cusps were individually ruptured or cut, and the wall of the vein painstakingly sewn closed. Later, a variety of push- or pull-through devices were tried, tearing or disrupting the valve cusps as the devices passed and thereby avoiding extensive surgery. The simplest of such devices was a blunt tip on a flexible plastic rod that was pushed down the vein from above. The obstructing valve cusps were to be inverted or torn as the tip passed. In practice, however, it was noted that a sturdy valve cusp could redirect the blunt tip through the wall of the vein without disrupting the cusp.

Since most valves consist of two individual pocket-like cusps, a double-tipped device was later developed to be pulled from below with a flexible wire. This second device was a cylindrical body ending in two parallel points with a V-shaped gap between them. The wire, anchored at the center of the V, pulled the blunt tips into and through the valve cusps. The tearing force of such device however was largely transferred to the wall of the vein by the stressed cusp, and the sharp points operated dangerously close to the venous wall, hence the resulting wall trauma was implicated in subsequent poor results. In a further device, cutting blades were positioned between the points and wire. This was done to cut the cusps once they came into contact with the points, rather than tear the cusps from the wall. A significant problem here was presented by tributary veins which enter the main vein at all possible angles and locations. The favored angle presents a leading edge of vein wall (as will become apparent from the drawings below), increasing the likelihood that one of the instrument tips might enter the tributary vein instead of a valve cusp. The blade could then make a longitudinal cut down the wall of the main vein, with disastrous results.

Another "trailing-type" device involved a circular cone pulled from its point. The cone was followed by a space or gap and then a rounded piece of the same diameter as the cone base. Within the gap was a circular blade of a smaller diameter than the cone base. The pliable valve cusps were expected to intrude into the gap as the cone passed and be cut by the circular blade. The efficacy of cutting both cusps on a single pass of the instrument has not been described.

All of these earlier devices suffer from a number of significant problems. First, the saphenous vein tapers from a maximum diameter of about 8 mm to a minimum diameter of about 2 mm. Valve cusps along the vein have a proportional size range. Thus the ideal device is one that can be fully effective and non-traumatic to the vein wall at any vein diameter. None of the above devices were, often requiring many different sized instruments for one operation. Second, the internal surface of the vein wall is lined with a delicate film of tissue one-cell thick. This film is easily stripped, and the exposed inner surface initiates blood clotting. Given the actual and potential vein wall trauma, it has been recommended that all devices similar to the ones described be abandoned.

To date, no pull-through valvulotome device has gained wide acceptance. The standard today involves actual cutting mechanisms. One device used mounts a scissor on a long slender rod, which is inserted down the vein to cut the valve cusps. Great care must be taken to avoid damage to the vein wall. Another device is a short curved blade with a blunt tip, affixed and oriented at a right angle to a slender rod. In both function and appearance it is similar to a crochet hook. The device is inserted through a tributary vein from below the valve and passed above the valve cusps; on withdrawal, it hooks and then cuts the valve cusps. Again, great care must be used to avoid damage to the vein wall. As tributary vein openings frequently are located near or even within the region of the cusps, the further hazard of hooking the leading edge of the vein wall is again presented. Furthermore, in both of the procedures described, exposure of the entire vein to direct view is considered a requirement. This involves a skin incision and local vein dissection for the entire length of the proposed vein conduit, an incision that potentially reaches from the groin to the ankle. Some trauma to the vein is inevitable, which again can lead to blood clotting in the bypass conduit and eventual failure of the surgical procedure.

BRIEF DESCRIPTION OF THE INVENTION

The present invention comprises a surgical device for safely disrupting vein valve cusps, to prepare the vein (particularly the saphenous vein of the leg) for an in-situ vein bypass graft. The device comprises three main portions, including (i) a manual, remote control assembly, e.g., a plunger and barrel syringe-like handle, at a proximal end, (ii) a slender, flexible cannula extending from the handle and preferably having at the distal end thereof a steel sleeve with an annular ridge, and (iii) any number of fine flexible steel wires running through the cannula, each wire having a hooked-end portion for engaging, and piercing, a valve cusp. The wires are protractable beyond the tip of the cannula into an open position wherein their free ends flare outwardly toward the vein wall from which the cusps extend, fully exposing their hooks and positioning them to ensnare valve cusps. Conversely, when the wires are retracted, they are drawn together within the cannula, leaving only their hooks situated outside, and resting against, the end of the cannula. In use, the cannula is first inserted in the retracted postion up the saphenous vein from the distal anastomotic site or from a tributory vein. The working grasping end is positioned just above the valve cusps using radiologic techniques or direct vision of the vein exterior. Alternatively the instrument is fully inserted up the vein and the wire protracted to open the hooks slightly. As the instrument is withdrawn, the lip of a valve cusp will be guided into the hook opening, halting the instrument's progress and precisely locating the valve without other invasive techniques. With hooks stationary, the canula is advanced up the hook wires, thereby drawing the hooks to a central position and covering their sharp ends. A slight tub on the instrument then disrupts the cusps. The procedure is repeated as the valvulotome is withdrawn down the length of vein until all valves have been disrupted, thus preparing the vein for grafting.

DETAILED DESCRIPTION OF THE DRAWINGS

Figures 1, 1A:
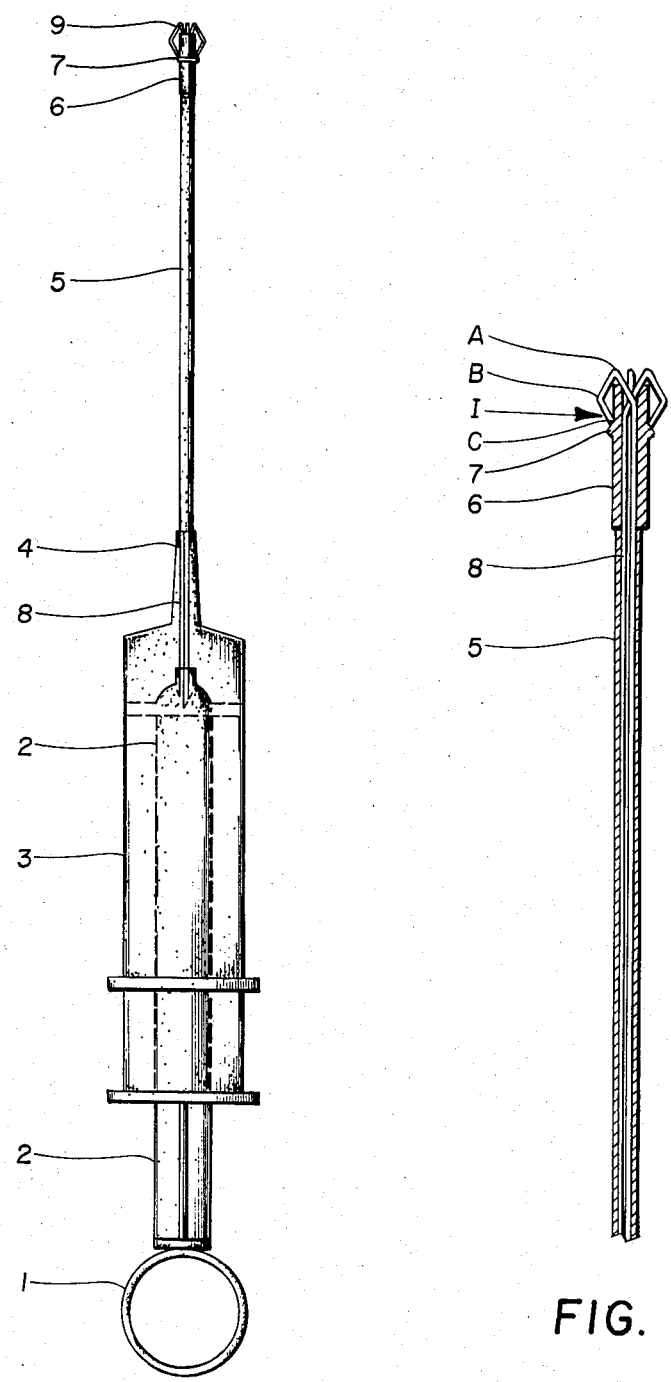
FIG. 1 is a side view of one embodiment of the present invention showing the wires in the closed position.
FIG. 1A is an enlarged, cross-sectional view of the distal tip of FIG. 1.

FIG. 1 shows a side view of a preferred embodiment of the valvulotome of the present invention, with its wires in the closed, retracted position. Finger ring 1 and attached slidable shaft 2 together form the plunger portion of the syringe-type handle, by means of which the valvulotome is manually controlled remote from the vein site, outside the patient's body. Barrel 3, in which shaft 2 slides axially (as seen in phantom), is attached via collar 4 to cannula 5, a narrow, flexible guide tube with a diameter small enough to fit easily within the lumen of the saphenous vein without contacting the interior walls of the vein, and which preferably has at the distal end thereof steel sleeve 6. Sleeve 6 as shown is approximately 10 mm in length, and preferably formed with fine annular ridge 7. Lastly in FIG. 1 are pictured hooked-ends 9 of wires 8 that run lengthwise within cannula 5 and which are attached to the handle at the distal end of shaft 2. The wires are preferably spirally bound within the cannula, although remaining free toward their distal ends so as to retain their natural spring. The device of FIGS. 1-6 utilizes 3 substantially identical wires posed roughly symmetrically within the cannula, although any number of wires may be used. Both sleeve 6 and wires 8 are preferably made of a fine gauge surgical stainless steel, although in the case of the sleeve any surgical material offering an inflexible end would be suitable. The guide tube is preferably made of a flexible, resilient synthetic material commonly used in surgical cannulae, and should be particularly fatigue-resistant. While the guide tube is preferably less than 2 mm in diameter so as to be operable throughout the saphenous vein, whose diameter varies from approximately 2 to 10 mm, the valvulotome can be made on a greater scale as well.

FIG. 1A offers an enlarged view of the distal end of the valvulotome of FIG. 1, in cross-section, showing wires 8 in the retracted or closed position within cannula 5, with hooked-ends 9 drawn together at the cannula's tip and pressed against the exterior of steel sleeve 6. In this closed position, hooks 9 remain outside, with the tip of each hook pressed against annular ridge 7 of sleeve 6, sealing off the opening of the hook in this position. As can be seen in FIG. 1A, annular ridge 7 is situated at a distance from the distal rim of sleeve 6 that is equal to the length of side AC of triangle ABC formed by these structures in the closed position, which in turn is equal to the distance between the vertex of wire 8 and the tip of hook 9 when the valvulotome is in the closed position. The valvulotome can also operate without annular ridge 7, though perhaps with less facility. Although the hooked-ends are shown in a roughly triangular configuration in the described embodiment, such hooks can include arcuate or straight segments.

Figures 2, 2A:
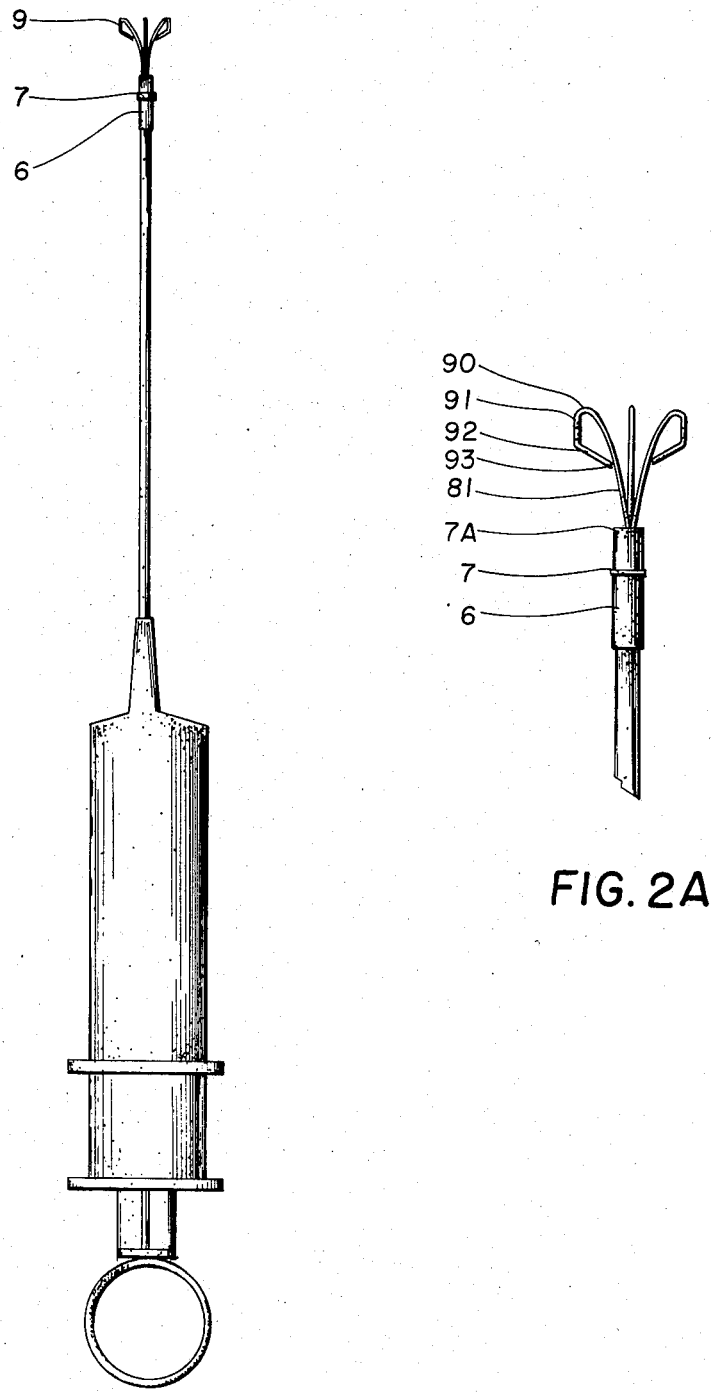
FIG. 2 is a side view of the embodiment of FIG. 1 showing the wires in an open position.
FIG. 2A is an enlarged view of the distal tip of FIG. 2.

FIG. 2 shows a similar view of the valvulotome as in FIG. 1, except that wires 8 are extended beyond the distal end of cannula 5 into an open position, with wires 8 slightly flared bringing hooked-ends 9 out to a point beyond the diameter of cannula 5. To achieve this open position, finger ring 1 and integral shaft 2 are advanced slightly up barrel 3, which in turn advances wires 8, whose springy steel ends naturally bow when unrestrained. The further the wires are advanced beyond cannula 5, the more they will bow outward, and slightly downward as directed by their arched or hooked-ends, ultimately making contact with a surrounding vein wall. It is this action of the wires originating within the cannula which allows the valvulotome to be adjusted out to any vein diameter; it is the specific configuration of hooked-ends 9 which protects the vein wall from trauma while assuring the subsequent engagement of each valve cusp. These, as well as other features of the present invention will be discussed in greater detail below.

FIG. 2A, an enlargement of the top portion of FIG. 2, reveals further detail of hooked-ends 9 of wires 8 in the open position. Each wire 8 is bent back over itself in such a manner as to form sides 91 and 92 as well as narrow gap 93 between the main stem of each wire 8 and the tip of its hook. It can be seen that in this open, flared position, only sides 91 of hooked-ends 9 would contact a surrounding vein wall, doing so from an orientation substantially parallel with the wall, thereby insulating it from any sharp edges or points. Simultaneously, gap 93 is directed away from the wall and down toward the main stem of wire 8, further guarding against accidental nicking of the vein wall. Due to the slenderness of cannula 5, the valvulotome need make no other contact with the vein wall, as will be better understood from the remaining drawings.

Figure 3:
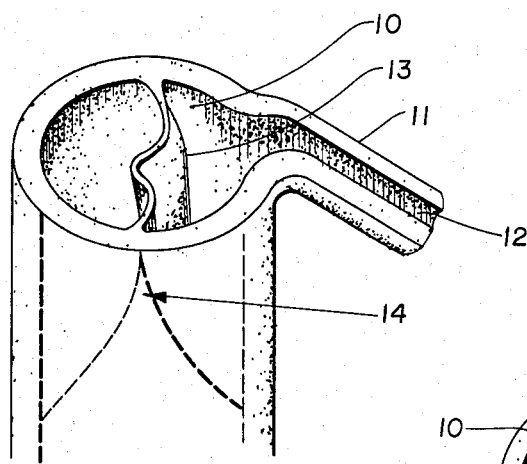
FIG. 3 is cross-sectional perspective view of a typical valve site in a vein.

FIG. 3–6A depict, in sequence, the operation of the present invention on a vein valve. FIG. 3 shows a vein section into which the valvulotome is introduced, including interior vein wall 10, valve cusps 13, tributary vein 11, tributary vertex 12, and path 14 between the individual valve cusps shown in their closed, valve-operative position.

Figure 3A:
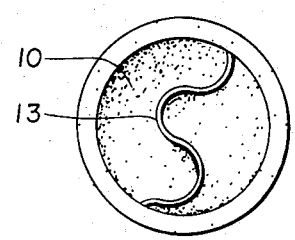
FIG. 3A is a cross-sectional view from above of the site of FIG. 3.

FIG. 3A shows a horizontal cross-section of this site from above. In operation, an incision is made in the saphenous vein, usually near the ankle where the saphenous vein is narrowest or in a tributary vein. Cannula 5, with wires 8 in the closed position of FIG. 1, is then inserted up the vein. In such closed position, most advantageously the diameter at the widest section of this distal end (i.e., through axis I—I of FIG. IA) would be roughly 2 mm, but could be up to 4 mm. The configuration of hooked-ends 9, and the natural contours of the valve cusps (i.e., like a baggy pocket, attached along the bottom and sides, but with a redundant amount of pocket material toward the opening) are such that cannula 5 glides easily up path 14 between the individual cusp walls. Also, in the closed position gaps 93 of hooks 9 are sealed off by the connection of hook tip C and annular ridge 7, and the resultant closed configuration allows the valvulotome to move up and down freely in the valved vein. Hence, all hooking, piercing and rupturing of valve cusps is fully controlled; the instrument can be returned to this valve-neutral position at any time, and withdrawn without further interruption of encountered valve cusps.

Figure 4:
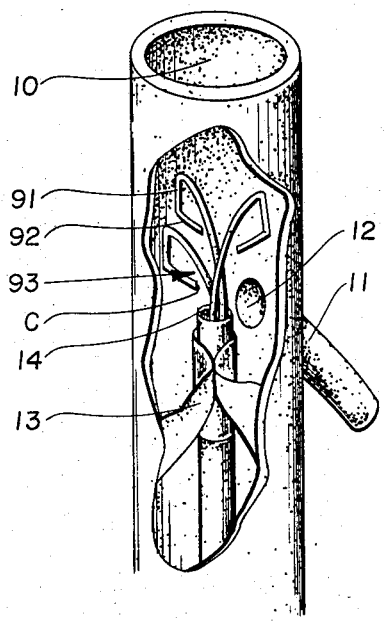
FIG. 4 is a side cutaway view of a vein valve site of FIG. 3, additionally showing the embodiment of FIG. 2 introduced into the vein and poised for valve engagement.
Figure 4A:
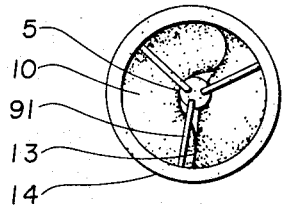
FIG. 4A is a cross-sectional view from above of the site of FIG. 4.

Once the valvulotome is inserted, it is obviously necessary to locate the valve sites in order to remove each set of valve cusps individually. Such valve sites can be located basically in three ways: (1) by direct visualization, for which it is necessary to view the entire length of vein, requiring more extensive surgery; (2) radiographically, requiring the use of radiologic dyes; and (3) by sensory location with a surgical device. With the present invention, this last, least intrusive alternative can be achieved by first protracting the wires into a partially open position to open gap 93 of hook 9 slightly, though without fully extending hooks 9 out to vein wall 10. The instrument is then gradually withdrawn down the vein, opposite the direction of first insertion, until a set of valve cusps is encountered, i.e., a slight resistance is palpably transmitted back to the manual control of the valvulotome as the lip of a cusp is snagged within gap 93. Commonly there are two cusps per valve at each valve site. Advancement of finger ring 1 (FIG. 1) will then extend hooks 9 beyond cannula 5, causing the distal ends of wire 8, and consequently hooks 9, to flare laterally toward vein wall 10 into a fully open position, as shown generally in FIG. 4. The flexibility of the flared portion of wire 8 allows the working hooks to conform to the inner diameter of the vein. No danger is presented to the vein wall by the unlikely event of overadvancement of the wires, due to their shape and high degree of deformability. It can be appreciated from FIG. 4 that sides 91 of hooked-ends 9 are substantially parallel to vein wall 10 in this fully open position, and that the tip of each hook at the free-end of sides 92 is pointed downward toward sleeve 7 at an angle of approximately 30° to the vein wall. The instrument is then withdrawn gradually down the vein until cusps 13 are engaged by hooked-ends 9, the free, upper edge of each cusp being guided directly into gap 93. The diminutive size of gap 93, as well as its position at the base of angled side 92, protects against accidental hooking of the leading edge of a tributary vein (illustrated in FIGS. 3 and 4 by 12) and any subsequent tearing of the vein wall, a serious hazard of prior art devices. FIG. 4A shows the valvulotome of the present invention in the same position as FIG. 4, but from a horizontal cross-sectional perspective.

Figure 5:
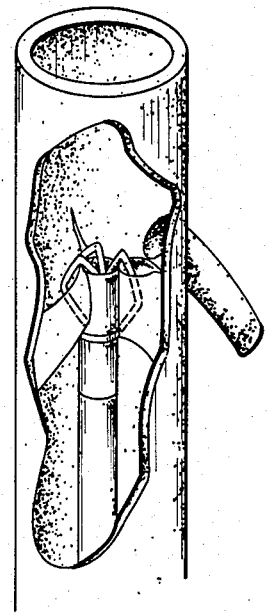
FIG. 5 is a side cutaway view of the site of FIG. 4, showing the embodiment of FIG. 1 in hooked engagement with the valve cusps.
Figure 5A:
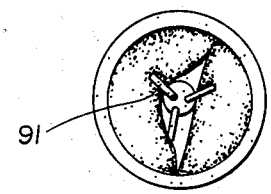
FIG. 5A is a cross-sectional view from above of the invention as positioned in FIG. 5.

Turning to FIG. 5, once cusps 13 are engaged by hooked-ends 9 as described above, barrel 3 and attached outer sleeve 5 are advanced up wires 8 while the finger ring 1 and attached wires 8 are held motionless against the resistance of the leading edge of cusp 13. This will retract wires 8 from the open position of FIG. 4 to the closed position of FIG. 5, simultaneously withdrawing the walls of each cusp more tautly into the center of the lumen, and locking them between sides 91, 92 of hooked-ends 9 and steel sleeve 6. In the present embodiment, hooked-ends 9 are drawn into a tight, three-wire rosette. FIG. 5A shows the valvulotome closed around engaged cusps 13 as in FIG. 5, but from above. In this closed position, the tip of the hook presses firmly against annular ridge 7, providing a ledge for piercing the delicate valve tissue ensnared therebetween. For this purpose, ridge 7 is preferably made of a yieldable substance, e.g., rubber, so that hook tip C can be urged into ridge 7 and thereby penetrate the intermediate valve tissue. However, even without the cooperation of ridge 7, hook tip C can puncture the valve. Simultaneously, the top edge, or lip, of valve cusp 13 is pressed between crook 90—the first bend in wire 8—and edge 7A at the distal end of steel sleeve 6. From this position, finger ring 1 and barrel 3 (FIGS. 1 and 2) are together urged downward, pulling the distal assembly down the vein and through the valve site, thereby disabling valve cusp 13. Thus it can be seen that this tearing action is done from the center of the lumen, avoiding any involvement of vein wall 10. Wall 10 is only momentarily contacted by parallel side 91 just prior to the capture of each cusp.

Figure 6:
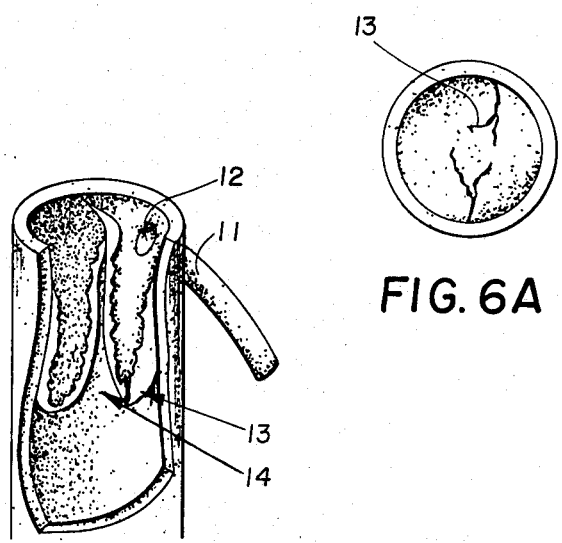
FIG. 6 is a side cutaway view of the vein valve site of FIG. 5, after the instrument of FIG. 1 has passed through the site.
Figure 6A:
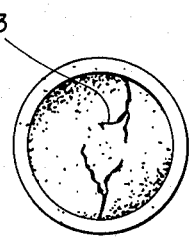
FIG. 6A is a cross-sectional view from above of the site of FIG. 6.

A pair of disrupted cusps is illustrated in FIG. 6, and again from an aerial view in FIG. 6A. The puncture of the exquisitely thin yet highly tensile cusps between the hook tip C and annular ridge 7 initiates a tear, and therefore much less force is required to produce the tear. Paradoxically due to the tapering size of the cusp in relation to its attachment to the firm vein wall, the tear propagates up the cusp as the instrument is drawn down through the valve site. This action interrupts each valve cusp approximately down its center. The remaining valve tissue folds back against wall 10 and the valvulotome continues down the vein in the partially-open position until the next set of valve cusps is encountered. The procedure is then repeated, until all valve cusps in the section of vein to be grafted are eliminated. Multiple passes through the vein will assure that no cusp remains even partially intact.

In particularly large and sturdy cusps, it may happen that the first pass of the valvulotome will tear an upper portion of the cusp, where due to the smaller reletive size of the hook there is direct contact with the hook mechanism, leaving some length toward the base of the cusp intact. In such a case, a further pass of the valvulotome from the fully open position will detect the remaining length of intact cusp, whose upper edge is now closer to vein wall 10, and tear it substantially to its base, destroying any residual integrity of the valve. In doing so, cannula 5 may be drawn away from the center of the lumen toward vein wall 10 when hooked-ends 9 are closed around the cusp, since no longer will there be a lot of redundant valve tissue extending out into the lumen. Nevertheless, the configuration of hooked-ends 9 will prevent any substantial contact between wall 10 and cannula 5, and more importantly between wall 10 and hook tip C, in this more proximate position.

It can be appreciated from the foregoing that the invention functions equally well in all diameters of vein, with a self adjusting ability or conformity to all vein diameters. The size of the cannula, and the configuration and manner of operation of the wires offer a degree of safety to the vein not heretofore provided in valvulotome devices without sacrificing efficacy. Its operation requires only an incision at vein graft sites, avoiding the further trauma of the extensive surgery to the vein itself. Finally, the entire instrument is simply and inexpensively made from common surgical materials, and is straightforward to operate.

What is claimed is:

1. An apparatus, for disabling valve cusps within a vein, comprising:
   (i) a flexible guide tube of a diameter substantially smaller than that of the vein so that the guide tube may be contained entirely within the lumen of the vein along the entire length of the vein, thus allowing minimal contact with the interior vein wall;
   (ii) hooking means, for ensnaring a valve cusp within the vein, including at least one springy wire retractably disposed within the guide tube for axial motion of such hooking means into first and second positions, such wire being configured at its distal end into a hook formation so as to have a main stem portion and a hooked portion including a vertex, a tip and a gap between the tip and the main stem portion, the gap of each hook being sufficiently small as to preclude entry therein of any venous structure substantially thicker than a valve cusp, the hooking means in the first position being retracted substantially entirely within the guide tube, with the hooked portion of the each wire resting just outside, and against, the distal end of the guide tube, and the tip of each hook being pressed against the guide tube so as to seal off the gap of the hook, such that the hooked portion of the hooking means assumes a configuration about the distal end of the guide tube which is sufficiently compact as to be contained entirely with the lumen of the vein along a substantial length of the vein without contacting the vein wall;
   the hooking means in the second position being retracted up the guide tube so as to expose a desired length of each wire beyond the distal end of the guide tube, and wherein such exposed length flares outwardly so as to bring a lateralmost surface of the hooked portion thereof into contact with the vein wall; and
   (iii) control means, attached to the guide tube and the hooking means, for controllably moving the hooking means axially within the guide tube.

2. An apparatus according to claim 1, wherein the distal end of each wire is configured so as to bring the lateralmost surface of each wire into substantially parallel position with the vein wall when such wire is in contact with such vein wall in the second position.

3. An apparatus according to claim 2, wherein the hooked portion includes at least one of arcuate and straight segments.

4. An apparatus according to claim 3, wherein the hook formation at the distal end of each wire is roughly triangular when the hooking means is in the second position, including a first side formed by a segment of the main stem portion, and second and third sides formed, respectively, by upper and lower segments of the hooked portion, and wherein the gap of the hook is positioned between the first and third sides.

5. An apparatus according to claim 3, wherein the third side is inclined back toward the first side at an acute angle.

6. An apparatus according to claim 4, wherein the third side is inclined back toward the first side at an angle of roughly 30°.

7. An apparatus according to claim 3, wherein the hook formation at the distal end of each wire is roughly triangular in the first position, including a first side formed by a distalmost length of the guide tube, and second and third sides, respectively, formed by upper and lower segments of the hooked portion.

8. An apparatus according to claim 7, further comprising an annular ridge disposed parallel to the distal edge of the guide tube, such that in the first position the tip of each hook is pressed against the annular ridge for piercing a valve cusp ensnared between such tip and such ridge.

9. An apparatus according to claim 3, wherein the mechanical disruption of the valve cusps occurs in the lumen of the vein, remote from the vein wall.

10. An apparatus according to claim 9, wherein the hook formation is roughly triangular, including a first side formed by a distalmost segment of a main, elongate stem of the wire, and second and third sides, respectively, formed by upper and lower segments resulting from consecutive bends in the wire and wherein the gap of the hook is defined between the first and third sides.

11. An apparatus according to claim 10, wherein the third side of the triangular hook is obliquely inclined back toward the main, elongate stem of the wire.

12. An apparatus according to claim 11, wherein the third side is inclined back toward the main, elongate stem of the wire at an acute angle.

13. An apparatus according to claim 12 wherein the third side is inclined back toward the main, elongate stem of the wire at an acute angle of approximately 30°.

14. An apparatus according to claim 8, wherein the control means is manually operable.

* * * * *